(12) United States Patent
Eriksson et al.

(10) Patent No.: US 10,577,333 B2
(45) Date of Patent: Mar. 3, 2020

(54) TETRAZOLE DERIVATIVES AS CYTOCHROME P450 INHIBITORS

(71) Applicant: C26 Bioscience AB, Örebro (SE)

(72) Inventors: Leif Eriksson, Göteborg (SE); Allan Sirsjö, Örebro (SE); Åke Strid, Örebro (SE)

(73) Assignee: C26 Bioscience AB, Örebro (SE)

( * ) Notice: Subject to any disclaimer, the term of this patent is extended or adjusted under 35 U.S.C. 154(b) by 0 days.

(21) Appl. No.: 16/076,571

(22) PCT Filed: Feb. 10, 2017

(86) PCT No.: PCT/GB2017/050361
§ 371 (c)(1),
(2) Date: Aug. 8, 2018

(87) PCT Pub. No.: WO2017/137770
PCT Pub. Date: Aug. 17, 2017

(65) Prior Publication Data
US 2019/0040020 A1 Feb. 7, 2019

(30) Foreign Application Priority Data
Feb. 12, 2016 (GB) .................................. 1602572.8

(51) Int. Cl.
*C07D 257/04* (2006.01)
*A61K 31/41* (2006.01)
*A61K 45/06* (2006.01)
*A61L 31/16* (2006.01)

(52) U.S. Cl.
CPC ............ *C07D 257/04* (2013.01); *A61K 31/41* (2013.01); *A61K 45/06* (2013.01); *A61L 31/16* (2013.01)

(58) Field of Classification Search
None
See application file for complete search history.

(56) References Cited

U.S. PATENT DOCUMENTS 4,540,703 A 9/1985 Uchida et al.

FOREIGN PATENT DOCUMENTS

| EP | 0033095 | 8/1981 |
| WO | 2005115147 | 12/2005 |
| WO | 2009153566 | 12/2009 |

OTHER PUBLICATIONS

STN Registry (CN# 727658-78-8, entry date: Aug. 17, 2004).*
Nair et al. "The Thiol-Michael Addition Click Reaction: A Powerful and Widely Used Tool in Materials Chemistry" Chemistry of Materials, 26(1):724-744 (2014) (Abstract only).
International Search Report and the Written Opinion of the International Searching Authority corresponding to International Patent Application No. PCT/GB2017/050361 (11 pages) (dated May 9, 2017).

* cited by examiner

*Primary Examiner* — Bong-Sook Baek
(74) *Attorney, Agent, or Firm* — Myers Bigel, P.A.

(57) ABSTRACT

According to the invention there is provided a compound of formula I, wherein $R^1$ and $R^2$ have meanings given in the description, which compounds are useful in the treatment of skin disorders and other diseases.

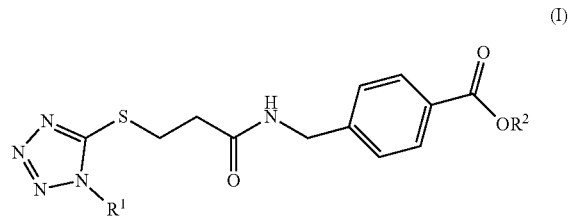

20 Claims, 5 Drawing Sheets

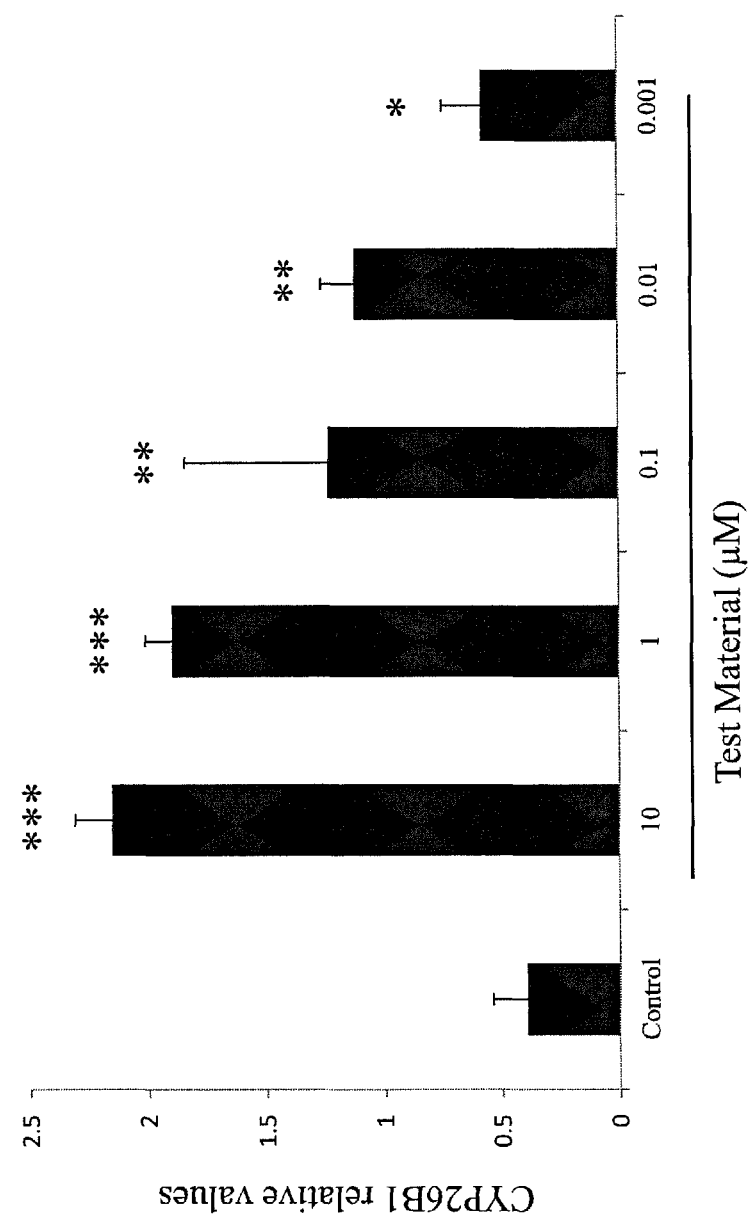

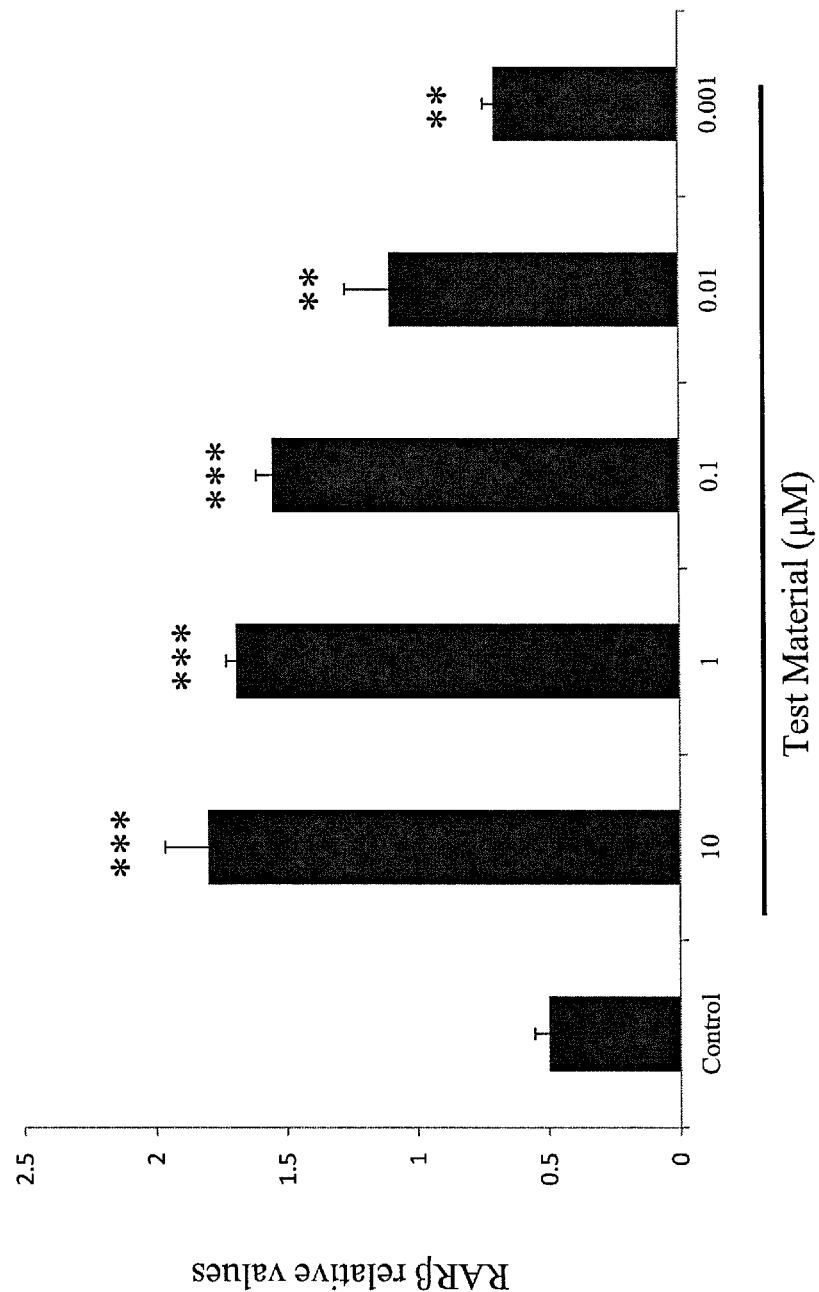

TETRAZOLE DERIVATIVES AS CYTOCHROME P450 INHIBITORS

FIELD OF THE INVENTION

Figure 2B:
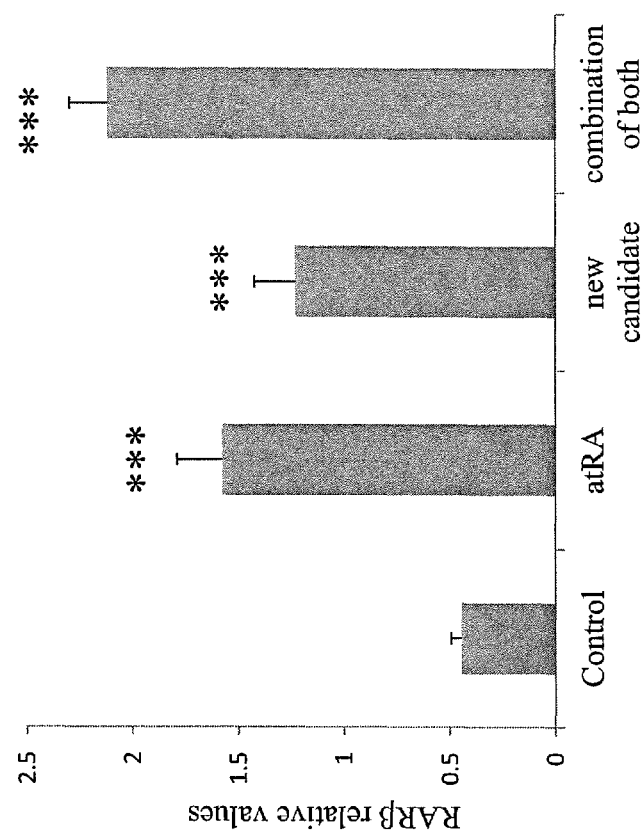

The present invention relates to new compounds and their use in medicine. More specifically, it relates to the use of compounds in the treatment of diseases and conditions in which a retained cellular level of endogenous all-trans retinoic acid (atRA) is beneficial through the inhibition of the enzyme CYP26B1 responsible for degradation of atRA.

BACKGROUND OF THE INVENTION

Retinoic acid (RA) is a critical signaling molecule in both embryonic development and in post-natal life. RA is the active metabolite of Vitamin A (retinol) and exists in several isoforms, of which all-trans RA (atRA), 13-cisRA and 9,13-dicisRA are those most commonly detected in the human body. Endogenous RA isomers are essential for stem cell and neuronal differentiation, in regulating insulin stimulated glucose secretion, in regulating cell cycles and apoptosis, and in the maintenance of healthy skin, epithelia and the immune system. A high level of cellular atRA has efficient antiproliferatory effects.

The biological activity of the RAs is mainly manifested by their binding to nuclear RA receptors (RARs), which leads to increased transcription of the target genes. The observed effects on gene transcription are thus dependent on cellular concentrations of atRA and on the expression levels of the three RAR isoforms. Catabolism of cellular atRA is achieved by members of the cytochrome P450 family 26 (CYP26), and in particular CYP26A1 in the liver and CYP26B1 in other adult human tissues. Inhibition of members of the CYP26 family may therefore provide a means to ensure elevated levels of endogenous atRA in the cells. Such inhibitors are referred to as retinoic acid metabolism blocking agents, RAMBAs.

A number of indications have been shown to lead to local up-regulation of atRA degrading enzymes and to respond favorably to treatment using exogenous atRA (or one of its isoforms) due to its ability to down-regulate cell proliferation.

These indications include dermatological conditions such as severe acne/rosacea, psoriasis, and keratinocytic ichthyosis. Synthetic vitamin A derivatives (retinoids) have long been the mainstay of treatment for several disorders of keratinization, notably the ichthyoses and severe acne. Some forms of psoriasis also respond well.

In terms of cosmetic anti-aging applications, prescribed creams containing atRA (intended for treatment of acne), are the only preparations with proven effect against fine lines and wrinkles.

Recent studies have shown that retinoic acid protects against intestinal inflammation mainly by shifting the Treg/Th17 profile, allowing for the treatment of inflammatory bowel diseases.

atRA has been successful in the chemotherapy treatment of various cancer forms such as neuroblastoma (NBI), acute promyelocytic leukaemia (APL), prostate cancer and to some extent post-menopausal breast cancer. One of the most impressive effects of atRA has been observed in the treatment of APL. Treatment of patients suffering from APL with high dose of atRA resulted in complete remission. Furthermore, several experiments in animals have demonstrated that atRA inhibited the induction and caused the disappearance of prostate tumors. In spite of these encouraging results, knowledge of the effects of prolonged atRA therapy on human cancers in the clinic has been scarce. It has been suggested that the therapeutic effects of atRA are undermined by its rapid in vivo metabolism and catabolism by cytochrome P450 enzymes (CYPs).

Emerging evidence, both clinical and molecular, indicates that retinoids may also be used to treat atherosclerotic lesions and restenosis phenomena in cardiovascular disease. Although the data from clinical trials examining the effect of vitamin A and vitamin A precursors on cardiac events have been contradictory, these data do suggest that retinoids do influence fundamental processes relevant to atherosclerosis. Preclinical cellular and animal model studies support these concepts. Retinoids exhibit complex effects on proliferation, growth, differentiation and migration of vascular smooth muscle cells (VSMC), including responses to injury and atherosclerosis. Retinoids also appear to exert important inhibitory effects on thrombosis and inflammatory responses relevant to atherogenesis. Recent studies suggest that retinoids may also be involved in vascular calcification and endothelial function, for example, by modulating nitric oxide pathways.

Treatment by addition of exogenous atRA or one of its isoforms is therefore often the main treatment or a co-treatment for these conditions.

Although atRA-treatment as such is a successful treatment modality, excessive intake of Vitamin A leads to a syndrome known as hypervitaminosis A or retinoic acid syndrome, characterized by erythema, weight and hair loss, bone pain, liver problems, build-up of fluid in lungs and in the rest of the body, kidney failure, skin and eye irritations, and teratogenicity. In addition, patients may also develop RA resistance during treatment.

To overcome these severe and unwanted side effects, the use of selective CYP26 inhibitors has been proposed, possibly together with mild addition of exogenous atRA. The most common and well-studied of these RAMBAs are ketoconazole, liarozole and talarozole. Albeit successful to varying degrees in cell tests, animal models, and clinical trials, their efficacy is not extraordinary. The main focus for all three RAMBAs has in this context been to target CYP26A1 for treatment of psoriasis, the rare disease keratinocytic ichthyosis, and prostate cancer.

The listing or discussion of an apparently prior-published document in this specification should not necessarily be taken as an acknowledgement that the document is part of the state of the art or is common general knowledge.

The inventors have surprisingly found that the compounds disclosed herein may be useful as inhibitors of CYP26, in particular the CYP26B1 isoform.

SUMMARY OF THE INVENTION

According to the present invention, there is provided a compound of formula I:

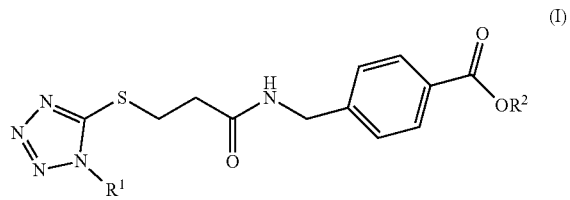

wherein:

$R^1$ represents hydrogen or $C_{1-2}$ alkyl, which alkyl group is optionally substituted by one or more fluorine atoms; and $R^2$ represents hydrogen or a carboxylic acid protecting group;

or a pharmaceutically acceptable salt thereof, provided that the compound or pharmaceutically acceptable salt thereof is not the compound of formula II:

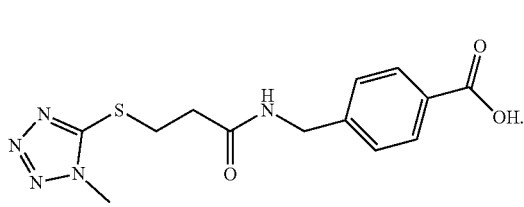

(II)

Pharmaceutically-acceptable salts that may be mentioned include acid addition salts and base addition salts. Such salts may be formed by conventional means, for example by reaction of a free acid or a free base form of a compound of formula I with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound of formula I in the form of a salt with another counter-ion, for example using a suitable ion exchange resin.

Examples of pharmaceutically acceptable addition salts include those derived from mineral acids, such as hydrochloric, hydrobromic, phosphoric, metaphosphoric, nitric and sulphuric acids; from organic acids, such as tartaric, acetic, citric, malic, lactic, fumaric, succinic, maleic, ascorbic, oleic, stearic, benzoic, glycolic, gluconic, succinic, arylsulphonic (e.g. tosylic), alkylsulfonic (e.g. mesylate) acids; and from metals such as sodium, magnesium, or preferably, potassium and calcium. Pharmaceutically-acceptable salts based on amines that may also be mentioned include ammonium and meglumine salts.

Compounds of formula I, as well as pharmaceutically-acceptable salts of such compounds are, for the sake of brevity, hereinafter referred to together as the "compounds of formula I".

Unless otherwise stated, the term "alkyl" refers to an unbranched or branched hydrocarbyl radical (such as ethyl, propyl, (e.g. n-propyl or isopropyl), butyl (e.g. n-butyl, sec-butyl, iso-butyl or tert-butyl) or, more preferably, methyl).

The term "carboxylic acid protecting group" refers to any group which is hydrolysable under physiological conditions to provide the compound of formula I in the carboxylic acid form. Examples of suitable carboxylic acid protecting groups include a $C_{1-4}$ alkyl group, phenyl and benzyl.

The use of protecting groups is described in "Protective Groups in Organic Chemistry", edited by J. W. F. McOmie, Plenum Press (1973), and "Protective Groups in Organic Synthesis", $3^{rd}$ edition, T. W. Greene & P. G. M. Wutz, Wiley-Interscience (1999).

The skilled person will appreciate that in certain preferred embodiments of the compounds of the invention, the proviso above will become redundant (for example, where it is stated that $R^1$ is a $C_{1-2}$ alkyl group substituted by one or more fluorine atoms, or $R^2$ is a group other than hydrogen).

In an embodiment of the invention, there is provided a compound of formula I wherein $R^1$ is a methyl group, optionally substituted by one or more fluorine atoms. For example, in a further embodiment, $R^1$ represents methyl or trifluoromethyl.

In an alternative embodiment, $R^1$ represents hydrogen, methyl or ethyl.

In a further embodiment of the invention, there is provided a compound of formula I wherein $R^2$ is a carboxylic acid protecting group (e.g. $R^2$ may represent methyl, tert-butyl or benzyl).

In another embodiment, $R^2$ represents hydrogen, a $C_{1-4}$ alkyl group, phenyl or a benzyl group (e.g. $R^2$ may represent hydrogen, methyl, tert-butyl or benzyl). In a further embodiment, $R^2$ represents methyl.

In embodiments in which $R^2$ may represent hydrogen (e.g. when $R^2$ represents hydrogen, a $C_{1-4}$ alkyl group, phenyl or a benzyl group), $R^1$ is preferably a $C_{1-2}$ alkyl group substituted by one or more fluorine atoms.

The compounds of the invention, as defined in Claim 1, do not include the compound of formula II. In an embodiment of the invention, the compounds of the invention include neither the compound of formula II nor a salt thereof.

Preferences and options for a given aspect, feature or parameter of the invention should, unless the context indicates otherwise, be regarded as having been disclosed in combination with any and all preferences and options for all other aspects, features and parameters of the invention. It should be appreciated that the invention may be embodied in different forms and should not be construed as limited to the embodiments set forth herein. Rather, these embodiments are provided so that this disclosure will be thorough and complete, and will fully convey the scope of the invention to those skilled in the art.

The skilled person will understand that terminology used in the description of the invention herein is for the purpose of describing particular embodiments only and is not intended to be limiting of the invention. Unless otherwise defined, all terms, including technical and scientific terms used in the description, have the same meaning as commonly understood by one of ordinary skill in the art to which this invention belongs.

As used in the description of the embodiments of the invention, the singular forms "a" "an" and "the" are intended to include the plural forms as well, unless the context clearly indicates otherwise. Thus, such references may be replaced with a reference to "one or more" (e.g. one) of the relevant component or integer.

As used herein, all references to "one or more" of a particular component or integer will be understood to refer to from one to a plurality (e.g. two, three or four) of such components or integers. It will be understood that references to "one or more" of a particular component or integer will include a particular reference to one such integer.

Also, as used herein, "and/or" refers to and encompasses any and all possible combinations of one or more of the associated listed items. Furthermore, the term "about," as used herein when referring to a measurable value such as an amount of a compound, dose, time, temperature, and the like, refers to variations of 20%, 10%, 5%, 1%, 0.5%, or even 0.1% of the specified amount.

When a range is employed (e.g. a range from x to y) it is it meant that the measurable value is a range from about x to about y, or any range therein, such as about $x_1$ to about $y_1$, etc.

It will be further understood that the terms "comprises" and/or "comprising," when used in this specification, specify the presence of stated features, integers, steps, operations, elements, components and/or groups thereof, but do not preclude the presence or addition of one or more other features, integers, steps, operations, elements, components, and/or groups thereof.

Compounds of formula I may be prepared in accordance with techniques that are well known to those skilled in the art, for example as described hereinafter.

Compounds of formula I may be prepared by a process which comprises reaction of a compound of formula III,

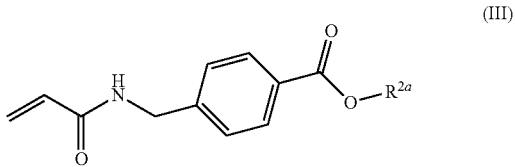

wherein $R^{2a}$ represents a suitable protecting group (e.g. as defined in respect of $R^2$), with a compound of formula IV,

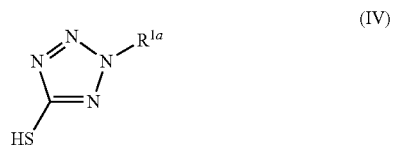

wherein $R^{1a}$ represents an alkyl group (e.g. in accordance with $R^1$) or a suitable nitrogen protecting group, such as benzyloxymethyl (BOM), under conditions that are known to those skilled in the art to be suitable for a Michael addition reaction, for example under the conditions described in D. P. Nair et al., Chem. Mater., 2014, 26 (1), pp 724-744. This reaction may be performed, for example, in the presence of a suitable base such as, LDA, BuLi, NaOH, KOH, $K_2CO_3$, $Et_3N$, $(i-Pr)_2NEt$, t-BuONa or t-BuOK (or mixtures thereof) in a suitable solvent such as dioxane, toluene, ethylene glycol dimethyl ether, dimethylsulfoxide, acetonitrile, tetrahydrofuran, dimethoxyethane (DME) or mixtures thereof. The reaction may also be carried out for example at room temperature or above (e.g. at a high temperature such as the reflux temperature of the solvent system).

Compounds of the invention bearing a carboxyester functional group (e.g. at $R^2$) may be converted into carboxylic acid derivatives through basic or acidic hydrolysis under conditions widely known in the art.

Medical and Pharmaceutical Uses

Compounds of formula I, including the compound of formula II, are indicated as pharmaceuticals. Therefore, according to a further aspect of the invention, there is provided a compound of Formula I, excluding the proviso, for use in medicine. For the avoidance of doubt, there is also provided a compound of Formula II for use in medicine.

The present invention provides a pharmaceutical formulation comprising a compound of formula I, excluding the proviso, or a pharmaceutically acceptable salt thereof, in admixture with a pharmaceutically acceptable adjuvant, diluent, excipient or carrier. In one embodiment, there is provided a pharmaceutical formulation comprising a compound of formula II, or a pharmaceutically acceptable salt thereof, in admixture with a pharmaceutically acceptable adjuvant, diluent, excipient or carrier.

In the context of medical and cosmetic applications, pharmaceutical formulations, combination medications, and the like, references to "the compounds of formula I" or "the compounds of the invention" include references to the compound of formula II, unless otherwise specified. In the medical and cosmetic applications discussed below, the compound of formula I may be any of the preferred compounds of formula I disclosed herein.

Advantageously, compounds of formula I excluding the proviso (i.e. including the compound of formula II) may be effective in selectively inhibiting the CYP26 family of enzymes, particularly CYP26B1.

The term "inhibit" may refer to any measurable reduction and/or prevention of catalytic activity of CYP26B1. The reduction and/or prevention of catalytic activity may be measured by comparing the activity in a sample containing a compound of the invention and an equivalent sample of CYP26 (e.g. CYP26B1) in the absence of a compound of the invention, as would be apparent to those skilled in the art. The measurable change may be objective (e.g. measurable by some test or marker, for example in an in vitro or in vivo assay or test, such as one described hereinafter, or otherwise another suitable assay or test known to those skilled in the art) or subjective (e.g. the subject gives an indication of or feels an effect).

As described above, the inhibition of CYP26 enzymes has been found to lead to an increase in the cellular level of endogenous all-trans retinoic acid.

Compounds of formula I excluding the proviso (i.e. including the compound of formula II) may, upon use, increase the levels of intracellular endogenous all-trans retinoic. An 4-6 fold increase in the level of intracellular endogenous all-trans retinoic has been shown to have positive effects on indications where elevated levels of all-trans retinoic acid is beneficial. Compounds of formula I excluding the proviso (i.e. including the compound of formula II) may also reduce degradation of exogeneously added all-trans retinoic acid.

According to a further embodiment of the invention, there is provided the use of a compound of formula I, excluding the proviso, or a pharmaceutically-acceptable salt thereof, for the manufacture of a medicament for the treatment of a condition in which an increase in the cellular level of endogenous all-trans retinoic acid, or a reduction in the degradation of exogeneously added all-trans retinoic acid, is desired or required.

There is also provided a compound of formula I, excluding the proviso, or a pharmaceutically-acceptable salt thereof, for use in the treatment of a condition in which an increase in the cellular level of endogenous all-trans retinoic acid or a reduction in the degradation of exogeneously added all-trans retinoic acid, is desired or required.

Still further, there is provided a method of treatment of a condition in which an increase in the cellular level of endogenous all-trans retinoic acid or a reduction in the degradation of exogeneously added all-trans retinoic acid, is desired or required, which method comprises administration of a therapeutically effective amount of a compound of Formula I, excluding the proviso, or a pharmaceutically acceptable salt thereof, to a subject in need thereof.

The present invention also provides a pharmaceutical formulation comprising a compound of formula I, excluding the proviso, or a pharmaceutically acceptable salt thereof, in admixture with a pharmaceutically acceptable adjuvant, diluent, excipient or carrier for use in the treatment of a condition in which an increase in the cellular level of endogenous all-trans retinoic acid or a reduction in the degradation of exogeneously added all-trans retinoic acid, is desired or required.

In one embodiment of the uses and methods of treatment described herein, the condition to be treated is one in which an increase in the cellular level of endogenous all-trans retinoic acid is desired or required.

In a further embodiment of the uses and methods of treatment described herein, the condition to be treated is one in which a reduction in the degradation of exogeneously added all-trans retinoic acid is desired or required.

In those aspects of the invention which relate to (i) the use of a compound of formula I, excluding the proviso, or a pharmaceutically-acceptable salt thereof, for the manufacture of a medicament as defined above; (ii) a compound of formula I, excluding the proviso, or a pharmaceutically-acceptable salt thereof, for use as defined above; or (iii) a method of treatment as defined above involving a therapeutically effective amount of a compound of Formula I, excluding the proviso, or a pharmaceutically acceptable salt thereof, it is preferred that the compound of formula I, or the pharmaceutically-acceptable salt thereof, is a compound of formula II, or a pharmaceutically-acceptable salt thereof.

The human or animal abnormalities and disorders which may be treated according to the present invention include any malignant, pre-malignant and non-malignant abnormalities or disorders responsive to increased levels of atRA or blocked catabolism thereof, such as, certain cancer forms, skin disorders such as psoriasis or actinic keratoses and acne, skin abrasions, keratinocytic ichthyosis, sundamaged skin, unwanted growth of damaged vessels relating to arteriosclerosis, and other diseases or infections. The term "disorders or abnormalities" is used herein as also comprising medical imbalances, diseases, and syndromes as well as bacterial and viral infections.

Therefore, the condition in which an increase in the cellular level of endogenous all-trans retinoic acid is desired or required may be one or more selected from a skin disorder, an undesirable growth or proliferation of cells, and restenosis or thrombosis occurring upon the introduction of coronary stents.

The compounds of the invention may also be useful in enhancing immune regulatory activity in the human intestinal tissue through inhibition of atRA catabolism, and may therefore be useful in the treatment of inflammatory bowel disease. Therefore, the condition in which an increase in the cellular level of endogenous all-trans retinoic acid is desired or required may also be inflammatory bowel disease.

Therefore, according to a further embodiment, there is provided the use of a compound of formula I, excluding the proviso, or a pharmaceutically-acceptable salt thereof, for the manufacture of a medicament for the treatment of a condition selected from a skin disorder; an undesirable growth or proliferation of cells; restenosis or thrombosis occurring upon the introduction of coronary stents; and inflammatory bowel disease. In such embodiments, it is preferred that the compound of formula I, or the pharmaceutically-acceptable salt thereof, is a compound of formula II, or a pharmaceutically-acceptable salt thereof.

Particular skin disorders that may be mentioned in this respect include, but are not limited to, psoriasis, vitiligo, severe acne, rosacea, and aging skin. In some embodiments, references to the treatment of skin disorders include the provision of skin benefits. Thus the compounds of the invention may be useful in providing skin benefits (preferably in a human). The term "skin benefits" is used herein to refer to one or more desirable effects on skin, including general improvements in skin health. Skin benefits include, for example, one or more of: increased firmness, increased elasticity, increased tonicity, and particularly reduced wrinkles (including reduced wrinkle width and/or volume). In particular embodiments which relate to the improvement in skin health, the use or method may be a therapeutic use or a therapeutic method.

The compound of formula I, excluding the proviso, or a pharmaceutically-acceptable salt thereof, may also be useful in cosmetic methods of improving skin health. According to a further aspect of the invention, there is therefore provided the use of a compound of formula I, excluding the proviso, or a pharmaceutically-acceptable salt thereof, in a cosmetic method of improving skin health. Such uses involve the administration of the compound to a subject, preferably via topical application. The phrase "improving skin health" is used herein to refer to the improvements mentioned in connection with the term "skin benefits". For example, such improvements may include one or more of: increased firmness, increased elasticity, increased tonicity, and particularly reduced wrinkles (including reduced wrinkle width and/or volume).

In an embodiment of this aspect of the invention, the compound of formula I may be the compound of formula II, or a pharmaceutically-acceptable salt thereof.

The term "undesirable growth or proliferation of cells" includes non-cancerous conditions (including warts and particularly psoriasis), as well as cancers and/or tumours. Compounds of formula I are therefore indicated for use in the treatment of cancer.

According to a further embodiment of the invention, there is provided the use of a compound of formula I, excluding the proviso, or a pharmaceutically-acceptable salt or solvate, or a pharmaceutically functional derivative thereof for the manufacture of a medicament for the treatment of cancer.

The compounds of formula I may be useful in the treatment of both primary and metastatic cancers. The term "cancer" will be understood by those skilled in the art to include one or more diseases in the class of disorders that is characterized by uncontrolled division of cells and the ability of these cells to invade other tissues, either by direct growth into adjacent tissue through invasion, proliferation or by implantation into distant sites by metastasis.

In a preferred embodiment, compounds of formula I may be capable of inhibiting the proliferation of cancer cells. By "proliferation" we include an increase in the number and/or size of cancer cells.

Alternatively, or preferably in addition, compounds of formula I may be capable of inhibiting metastasis of cancer cells. By "metastasis" we mean the movement or migration (e.g. invasiveness) of cancer cells from a primary tumor site in the body of a subject to one or more other areas within the subject's body (where the cells can then form secondary tumors). Thus, in one embodiment the invention provides compounds and methods for inhibiting, in whole or in part, the formation of secondary tumors in a subject with cancer. It will be appreciated by skilled persons that the effect of a compound of formula I on "metastasis" is distinct from any effect such a compound may or may not have on cancer cell proliferation.

Advantageously, compounds of formula I may be capable of inhibiting the proliferation and/or metastasis of cancer cells selectively.

By "selectively" we mean that the compound inhibits the proliferation and/or metastasis of cancer cells to a greater extent than it modulates the function (e.g. proliferation) of non-cancer cells. Preferably, the compound inhibits the proliferation and/or metastasis of cancer cells only.

Compounds of formula I may be suitable for use in the treatment of any cancer type, including all tumors (non-solid and, preferably, solid tumors, such as carcinoma, adenoma, adenocarcinoma, blood cancer, irrespective of the organ). Particular examples of cancers and/or tumours that may be mentioned include, but are not limited to, acute promyelocytic leukemia, neuroblastoma, prostate cancer, and breast cancer. Preferred cancers and/or tumours that may be treated by the compounds disclosed herein are acute promyelocytic leukemia and neuroblastoma.

Compounds of formula I, excluding the proviso, may be useful in preventing restenosis and thrombosis in patients who receive a stent (e.g. a. coronary stent). In an embodiment of this aspect of the invention, a compound of formula I, excluding the proviso, may be used to provide a chemical coating for a drug-eluting stent.

Increased levels of retinoic acid are considered to be potentially capable of protecting against intestinal inflammation. Thus, compounds of formula I excluding the proviso may be suitable for use in the treatment of inflammatory bowel diseases.

For the avoidance of doubt, in the context of the present invention, the terms "treatment", "therapy" and "therapy method" include the therapeutic, or palliative, treatment of patients in need of, as well as the prophylactic treatment and/or diagnosis of patients which are susceptible to, the relevant disease states.

A "subject in need" of the methods of the invention can be a subject known to have or suspected of having any of the diseases mentioned herein (in particular any of the skin disorders or cancers mentioned herein).

Subjects suitable to be treated with compounds and formulations of the present invention as described herein include, but are not limited to, mammalian subjects. In some embodiments, the subject may be a human subject.

As used herein, references to a "subject" to be treated may be synonymous with a "patient", and vice versa. "Patients" include mammalian patients, particularly human patients.

The term "therapeutically effective" as used herein in reference to an amount or dose refers to an amount of a compound, composition and/or formulation of the invention that is sufficient to produce a desired effect, which can be a therapeutic and/or beneficial effect. Such an effective amount will vary with the age, general condition of the subject, the severity of the condition being treated, the particular agent administered, the duration of the treatment, the nature of any concurrent treatment, the pharmaceutically acceptable carrier used, and like factors within the knowledge and expertise of those skilled in the art. As appropriate, an effective amount in any individual case can be determined by one skilled in the art by reference to the pertinent texts and literature and/or by using routine experimentation.

The concentration of the compounds as described hereinbefore in the compositions, depends upon the nature of the compound, the composition, mode of administration, the condition to be treated and the patient and may be varied or adjusted according to choice. When a compound of formula I (e.g. a compound of formula II) is present in a pharmaceutical formulation, said compound is preferably present in an amount of from 0.01 to 90% by weight of the formulation, even more preferably in an amount of from 0.05 to 50% (e.g. 0.2 to 30%) by weight of the formulation, such as an amount of from 1 to 20% by weight of the formulation. Lower doses may be used when derivatives are prepared which are highly lipophilic, e.g. a concentration range of 0.01 to 10%, e.g. 0.02 to 1%, by weight of the formulation.

Alternatively, the concentration of the compound of formula I (e.g. the concentration of the compound of formula II) in the composition may be selected to be sufficient to result in blood serum levels that are in the range of from 1 pM to 1 mM in the patient. Preferably, the concentration of the compound of formula I in the composition is sufficient to result in a blood serum level in the range of from 1 nM to 20 µM, such as from 50 nM to 5 µM. In one embodiment, the concentration of the compound of formula I in the composition is sufficient to result in a blood serum level in the range of from about 10 µM to about 100 µM. In another embodiment, the concentration of the compound of formula I in the composition is sufficient to result in a blood serum level in the range of from about 100 pM to about 10 µM. Dosages in drug eluting stents may be chosen such that the resulting in blood serum serum levels achieved are in the range of from 1 pM to 1 mM in the patient. In one embodiment, dosages in drug eluting stents may be chosen such that the resulting in blood serum serum levels achieved are in the range of from 10 pM to 100 µM in the patient.

The formulations of the invention may be prepared in a conventional manner with one or more physiologically acceptable carriers or excipients, according to techniques well known in the art. Where appropriate, compounds or compositions according to the invention are sterilized, e.g. by γ-irradiation, autoclaving or heat sterilization, before or after the addition of a carrier or excipient, where applicable, to provide sterile formulations.

Formulations may be administered topically, orally or systemically, or in a form released from graft stents. Topical compositions may include conventional gels, creams, ointments, sprays, lotions, salves, sticks, soaps, powders, pessaries, aerosols, drops, solutions, patches, direct injection and any of the other conventional pharmaceutical forms in the art.

Ointments, gels and creams may, for example, be formulated with an aqueous or oily base with the addition of suitable thickening and/or gelling agents. Lotions may be formulated with an aqueous or oily base and will, in general, also contain one or more emulsifying, dispersing, suspending, thickening or colouring agents. Powders may be formed with the aid of any suitable powder base. Drops and solutions may be formulated with an aqueous or non-aqueous base also comprising one or more dispersing, solubilising or suspending agents. Aerosol sprays are conveniently delivered from pressurised packs, with the use of a suitable propellant. The compound may in a form for topical administration be provided in solid form, to be reconstituted with a solvent before or in conjunction with treatment. Providing the compound in solid form may improve its storage stability.

Alternatively, the formulations may be provided in a form adapted for oral or parenteral administration, for example by intradermal, subcutaneous, intraperitoneal, intratumoral, intracavitary, intraoccular or intravenous injection. Alternative pharmaceutical forms thus include plain or coated tablets, capsules, suspensions and solutions containing the compound or composition according to the invention, optionally together with one or more inert conventional carriers and/or diluents, such as corn starch, lactose, sucrose, microcrystalline cellulose, magnesium stearate, polyvinylpyrrolidone, citric acid, tartaric acid, water, water/ethanol, water/glycerol, water/sorbitol, water/polyethyleneglycol, propyleneglycol, stearylalcohol, carboxymethylcellulose or fatty substances such as hard fat or suitable mixtures thereof.

The formulations of the invention may additionally include lubricating agents, wetting agents, emulsifying agents, suspending agents, preserving agents, sweetening agents, flavouring agents, adsorption enhancers, e.g. surface penetrating agents as mentioned below, and the like. The formulations of the invention may be formulated so as to provide quick, sustained or delayed release of the compound after administration to the patient by employing procedures well known in the art. Solubilizing and/or stabilizing agents may also be used, e.g. cyclodextrins (CD) $\alpha$, $\beta$, $\gamma$ and HP-$\beta$ cyclodextrin. Formulations may be in any appropriate dosage form, for example as an emulsion or in liposomes, niosomes, microspheres, nanoparticles or the like, or as active component in graft stents. The compounds of the invention may then be absorbed to, incorporated in or bound to these forms.

Topical administration to inaccessible sites may be achieved by techniques known in the art, e.g. by the use of catheters or other appropriate drug delivery systems.

The pharmaceutical compositions according to the invention, as described herein, are suitable for use as a medicament, e.g. in the treatment of human or animal abnormalities or disorders of the body.

The internal and external body surfaces, herein also referred to as merely "tissue", which may be treated in accordance with the invention include the skin and all other epithelial and serosal surfaces, including for example mucosa, the linings of organs e.g. the respiratory, gastro-intestinal and genito-urinary tracts, and glands with ducts which empty onto such surfaces (e.g. liver, hair follicles with sebaceous glands, mammary glands, salivary glands and seminal vesicles). In addition to the skin, such surfaces include for example the lining of the vagina, the endometrium and the urothelium. Such surfaces may also include cavities formed in the body following excision of diseased or cancerous tissue e.g. brain cavities following the excision of tumours such as gliomas. With 'surfaces' we herein also refer to the walls of blood vessels.

"Tissue" and "body fluid" are used herein as meaning any human or animal tissue and body fluid that may be treated, wholly or in part, or otherwise altered or affected by way of therapeutics based on inhibition of enzyme CYP26B1.

The surface-penetration assisting agent may be any of the skin-penetration assisting agents described in the pharmaceutical literature e.g. chelators (e.g. EDTA), surfactants (e.g. sodium dodecyl sulphate), non-surfactants, bile salts (e.g. sodium deoxycholate) and fatty acids (e.g. oleic acid). Examples of appropriate surface penetrating assisting agents include HPE-101 (available from Hisamitsu), DMSO and other dialkylsulphoxides, in particular n-decylmethylsulphoxide (NDMS), dimethylsulphacetamide, dimethylformamide (DMFA), dimethylacetamide, glycols, various pyrrolidone derivatives (Woodford et al., J. Toxicol. Cut. & Ocular Toxicology, 1986, 5: 167-177), and Azone™ (Stoughton et al., Drug Dpv. Ind. Pharm. 1983, 9: 725-744), or mixtures thereof. DMSO is, however, preferred due to its anti-histamine and anti-inflammatory activities.

The surface penetration agent may conveniently be provided in a concentration range of 0.2 to 50% (w/w), e.g. about 10% (w/w).

A pharmaceutical formulation comprising a compound of formula I (excluding the proviso) may additionally comprise one or more compounds selected from the group comprising of: chelating agents, inhibitors of ferrochelatase, immunotherapeutic agents, angiogenesis inhibitors, surface penetration assisting agents, photosensitising agents, glucose, anti-cancer agents (such as arsenic), anaesthetic or analgesic agents (including local anaesthetics such as prilocaine and lidocaine), retinoic acid and derivatives thereof, retinol and derivatives thereof, anti-inflammatory agents (including TNF-inhibitors, ustekinumab, NSAIDs and steroids), blood pressure reducing agents (such as beta-blockers and ACE inhibitors), cytostatic compounds, antibiotic agents (such as small band UVB agents), and folic acid antagonists (such as methotrexate).

Alternatively, or additionally, immunotherapy agents (e.g. antibodies or effectors such as macrophage activating factor), angiogenesis inhibitors, arsenic or other chemotherapy agents may be used to improve treatment according to the invention. Administration of these supplementary agents should be performed in terms of route, concentration and formulation, according to known methods for using these agents. These additional agents may be administered before, after or during administration of the current inhibitor, depending on their function. For example, angiogenesis inhibitors may be added 5 to 10 days after treatment to prevent tumor re-growth. In some cases the therapeutic effect for the combination will be synergistic.

Other anti-cancer agents may similarly be used in combination with a composition of the invention, either as part of the formulation or as a separate treatment to be administered simultaneously, separately or sequentially. A person skilled in the art, would have no difficulty determining the appropriate timing, sequence and dosages of administration for particular drugs and compounds of the present invention.

According to the condition being treated, and the nature of the composition, the compounds for use in the invention may be co-administered with such other optional agents, for example in a single composition or they may be administered sequentially or separately. Indeed, in many cases a particularly beneficial effect may be obtained by pre-treatment with the surface-penetration assisting agent in a separate step, prior to administration of the compounds for use in accordance with the invention.

In some situations a pre-treatment with a surface-penetration assisting agent, followed by administration of the CYP26B1 blocking agent in conjunction with the surface-penetration assisting agent may be beneficial. When a surface-penetration assisting agent is used in pre-treatment this may be used at high concentrations, e.g. up to 100% (w/w). In one embodiment, the method of the invention thus additionally comprises prior to the treatment a pre-treatment step with a surface-penetration assisting agent.

The invention thus provides a compound of formula I, excluding the proviso, or a pharmaceutically acceptable salt thereof, in combination with at least one surface-penetration assisting agent, and optionally one or more anti-cancer agents. The combination may be provided as a combined preparation for simultaneous, separate or sequential administration to the patient in order to treat disorders or abnormalities of external or internal surfaces of the body which are responsive to reduced metabolism of retinoic acid and derivatives.

According to one embodiment, the uses of the invention additionally comprise treatment with atRA or related derivatives thereof, whereby said compounds of formula I are administered simultaneously or prior to the administration of atRA to the patient.

As is mentioned elsewhere herein, the compounds of formula I, excluding the proviso, and pharmaceutically acceptable salts thereof, may be useful in preventing restenosis and thrombosis in patients who receive a stent (e.g. a coronary stent).

A further aspect of the present invention therefore provides a graft stent, a surface of which is at least partly coated with a compound of formula I as defined herein, excluding the proviso. Drug-eluting stents which may be mentioned in this respect include stents which would be known to the skilled person and which have been coated (at least partially) with a compound of the invention (or a pharmaceutically-acceptable salt thereof).

Drug-eluting stents typically consist of a stent platform, a coating, and one or more drugs. The stent itself is an expandable metal (or alloy) framework. The stents have elaborate mesh-like designs to allow expansion, flexibility, and in some cases the ability to make/enlarge side openings for side vessels.

The coating typically comprises a polymer and the drug. The polymer holds and elutes the drug into the arterial wall by contact transfer. Coatings are typically spray- or dip-coated. One to three or more layers can be used in the coating, e.g., a base layer for adhesion, a main layer for holding the drug, and sometimes a top coat to slow down the release of the drug and extend its effect.

Drug-eluting stents are inserted after percutaneous coronary intervention (PCI) of blood vessels, aiming to inhibit proliferation in the vessel wall. Proliferation in the damaged vessel wall is a major problem after insertion of stents. By coating stents with a compound of the invention (particularly the compound of formula II), or a pharmaceutically acceptable salt thereof, the coronary vessel can remain open to a greater extent. Without wishing to be bound by theory, it is believed that this effect is due to the indirect inhibition of proliferation that is achieved by the blocking of atRA metabolism by the compound of the invention.

Preferably, the amount of the compound of formula I in the stent coating is sufficient to achieve serum levels of between about 1 pM and about 1 mM in a patient. More preferably, the amount of the compound of formula I in the stent coating is sufficient to achieve serum levels of between about 10 pM and about 100 µM in a patient. Most preferably, the amount of the compound of formula I in the stent coating is sufficient to achieve serum levels of between about 100 pM and about 10 µM in a patient.

Graft stents of this type may be useful in the treatment of atherosclerosis in patients. The presence of the compound of formula I on a surface of the stent allows said compound to be delivered to the surrounding blood vessel walls where it is able to provide a therapeutic benefit. The delivery will predominantly occur via contact between the stent and the blood vessel wall. In addition, a portion of the compound of formula I may disperse into the blood stream of the patient whereby it is able to provide a therapeutic benefit to neighbouring regions of blood vessel walls.

Therefore, in a further aspect of the invention, there is provided a method of inhibiting restenosis following treatment of atherosclerosis in a patient, which method involves applying a graft stent, a surface of which is at least partly coated with a compound of formula I as defined herein, excluding the proviso, to a patient in need thereof. Surgical methods for applying stents are well known. In such methods, the graft stent is introduced in a collapsed form into an affected blood vessel in a patient, at which point the stent is expanded so that it opens up the lumen of the blood vessel and holds the blood vessel in the open form.

Similarly there is provided the use of a compound of formula I, as defined herein, excluding the proviso, in the coating of a drug eluting stent.

FIGURES

The following drawings are provided to illustrate various aspects of the present inventive concept and are not intended to limit the scope of the present invention unless specified herein.

For the data shown in FIGS. 1 to 4, the test compound was the compound of formula II.

FIG. 1 illustrates the induction of CYP26B1 and RARβ mRNA at different concentrations of test compound: A) CYP26 and B) RARβ in human smooth muscle cells treated with 0.001-10 µM of the test compound. For all experiments n=3; *$P \leq 0.05$, $P < 0.01$ and *$P < 0.001$.

FIG. 2 are diagrams of CYP26B1 and RARβ mRNA expression in human smooth muscle cells upon treatment with atRA and/or test compound: A) CYP26B1 and B) RARβ mRNA expression in human smooth muscle cells treated with either 1 µm of atRA, test compound or combination of both for 48 h. The experiment was performed in three independent runs; *$P \leq 0.05$, $P < 0.01$ and *$P < 0.001$.

FIG. 3 illustrates quantification of atRA levels by HPLC in human smooth muscle cells and transfected COS-1 cells: A) Human smooth muscle cells were treated with 1 or 10 µM of the new CYP26 inhibitor for 1 h followed by a 4 h [$^3$H] atRA incubation. B) COS-1 transfected by 1 µg/µL of CYP26B1 and incubated with 1 or 10 µM of test compound followed by a 2 h [$^3$H] atRA incubation. For all experiments n=3; *$P < 0.05$, $P < 0.01$ and *$P < 0.001$.

Figure 4:
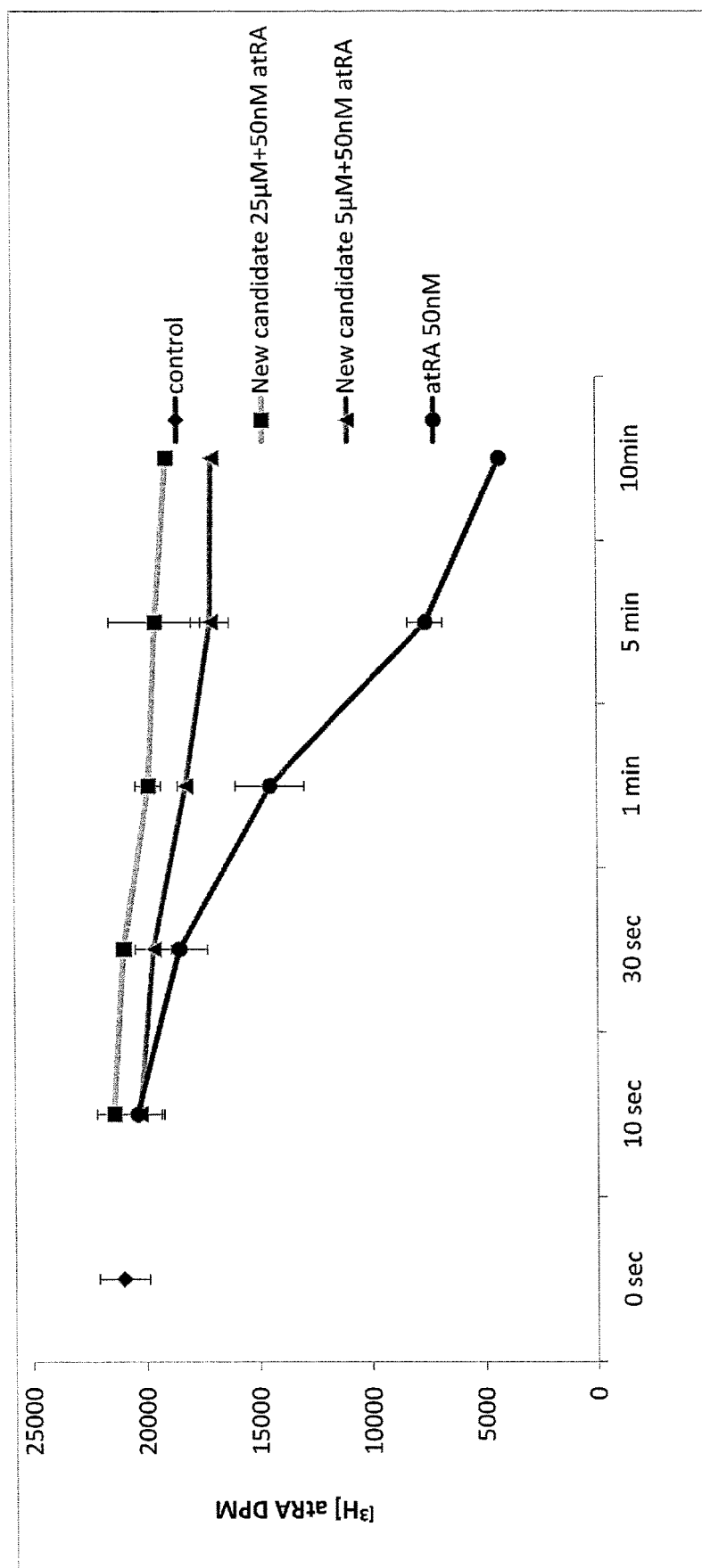

FIG. 4 is a graph showing results from an enzymatic assay carried out on purified CYP26B1, incubated with 5 or 25 µM of the test compound in the presence of oxidoreductase and NADPH, at different time points. The control experiment was performed without initiation with NADPH. For all experiments n=3.

EXAMPLES

The invention is illustrated by the following examples, in which the following abbreviations may be employed:
AOSMC Human aortic smooth muscle cells
atRA all trans-retinoic acid
COS-1 Fibroblast cell type (COS: CV-1 (simian) in Origin, and carrying the SV40 genetic material)
RA retinoic acid
RAR retinoic acid receptor For the experiments discussed below, independent two-tailed (Student's t test) and one way ANOVA was used for data analysis and all experiments were carried out at minimum three times and results were represented as mean±SD. The P-value considered being statistically significant at $P \leq 0.05$.

Preparation Method 1

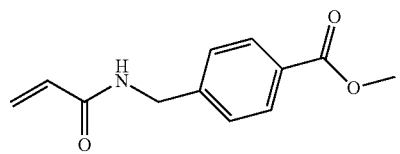 [SMILES: C=CC(=O)NCc1ccc(C(=O)OC)cc1]

4-(Aminomethyl)benzoic acid (methyl ester) is reacted with acrylic acid in the presence of PCl₃ to form the desired amide product.

Preparation Method 2

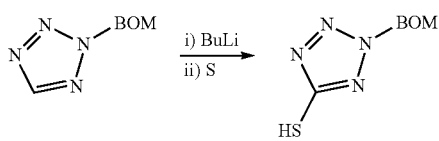

Butyl lithium is added to a solution of 2-N-benzyloxymethyl (BOM) tetrazole in ether. The resulting mixture is stirred before being quenched with sulphur to produce the thiol product.

Example 1

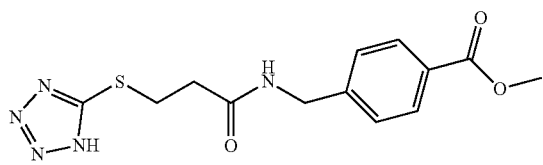 [SMILES: COC(=O)c1ccc(CNC(=O)CCSc2nnn[nH]2)cc1]

The amide obtained in Preparation Method 1 is reacted with the thiol obtained in Preparation Method 2 to form a BOM protected thioether product. The protecting BOM group is removed by reaction with hydrogen over a Pd(OAc)₂ catalyst.

Example 2

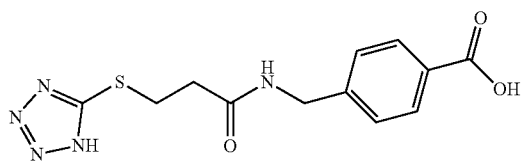 [SMILES: O=C(CCSc1nnn[nH]1)NCc1ccc(C(=O)O)cc1]

To a solution containing the product of Example 1 is added an acid. The resulting mixture is then heated to allow the ester group to hydrolyse and form the carboxylic acid.

Example 3. Effects of the Compound of Formula II on the Levels of atRA Responsive Genes CYP26B1 and RARβ

Human aortic smooth muscle cells (AOSMCs) were treated with different concentrations of a compound of Formula II (0.001-10 μM; FIGS. 1A and B). AOSMCs were incubated with different concentration (0.001-10 μM) of compound according to Formula II, or DMSO as control, at 37 C for 24 h. Total RNA were isolated by using E.Z.N.A total RNA kit (VWR Stockholm Sweden) and cDNA synthesis was performed through high capacity reverse transcription kits (applied Biosystems, Foster City, Calif., USA) according to manufacturers instructions. QRT-PCR was carried out for CYP26B1, RARβ, and Cyclophilin A (applied Biosystems, Foster City, Calif., USA) on 7900 HT fast real time PCR system (applied Biosystems, Foster City, Calif., USA), and the obtained values normalized to Cyclophilin A. The expression of CYP26B1 and RARβ mRNA was significantly induced in a dose-dependent manner. Similar results were obtained after treatment of endothelial cells.

Figure 2A:
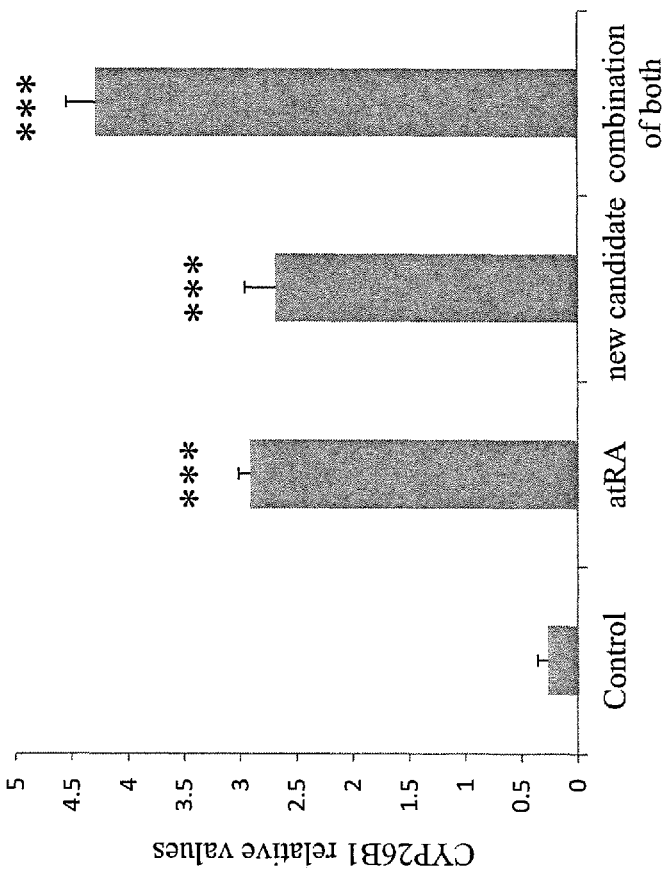

Next, human AOSMCs were treated with either 1 μM of atRA or a compound of Formula II alone, or a combination of both for 48 h. The purification and analysis procedures were as described above. The compound of Formula II significantly increased the effects of atRA on the induction of both CYP26B1 and RARβ mRNA (FIGS. 2A and B). The results strongly indicate that the compound of Formula II increases retinoid signalling.

Figure 3A:
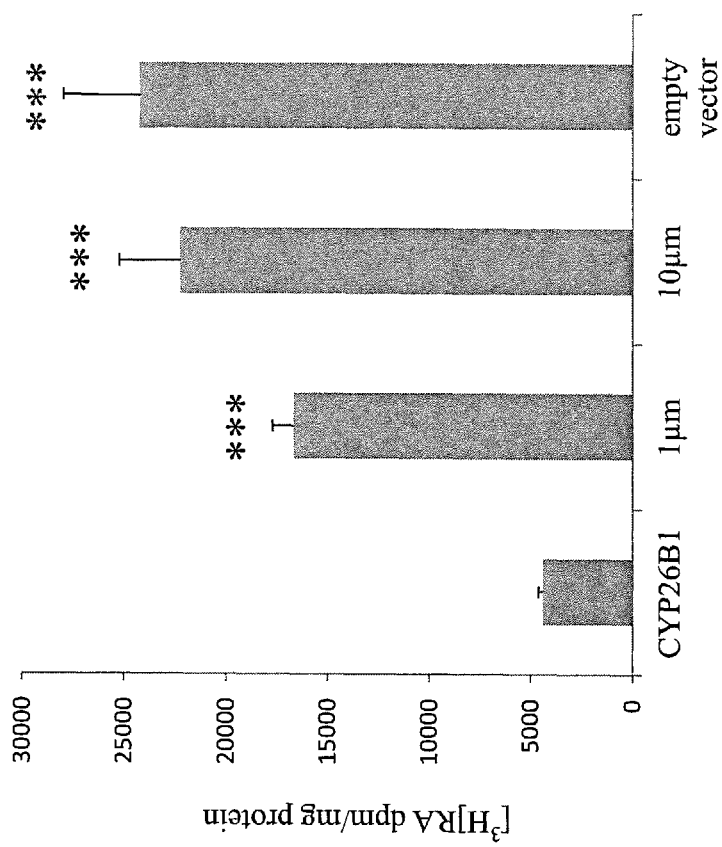
Figure 3B:
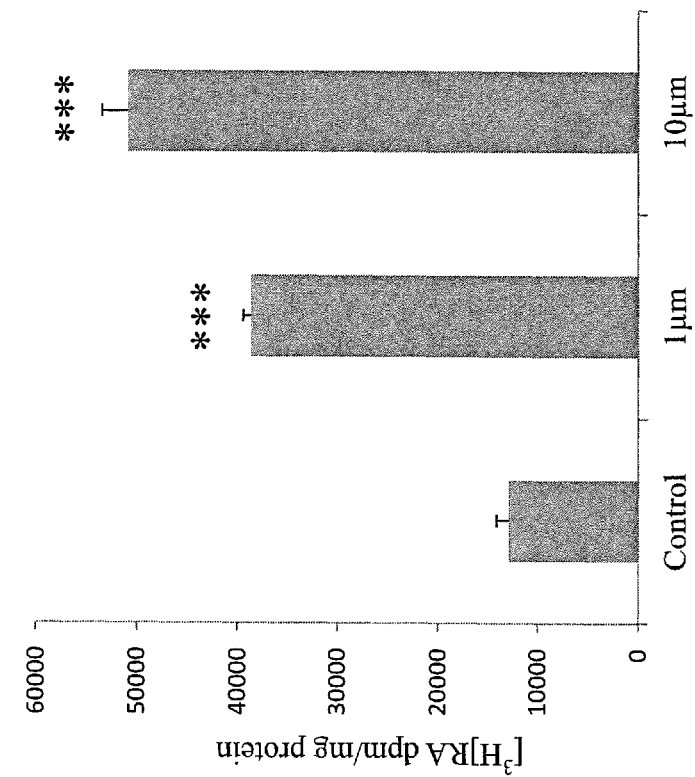

Example 4. Efficiency of the Compound of Formula II in Inhibition of atRA Catabolism by CYP26B1 in Human Smooth Muscle Cells and in CYP26B1 Transfected COS-Cells To demonstrate the effect of the compound of Formula II on RA catabolism by CYP26B1 human smooth muscle cells were treated with 1 or 10 μM of the inhibitor for 1 hour followed by 4 hour incubation with [³H] atRA ([³H] atRA obtained from Perkin-Elmer Life and Analytical Sciences, Boston, Mass., USA). AOSMCs were seeded out in density of 2×10⁵ in 6 well plates incubated with two different concentrations (1 and 10 μM) of compound according to Formula II for 1 h followed by exposure to 1 μCl/ml of [³H] atRA for 4 h. Cells were thereafter washed using BSA 1 mg/ml of PBS followed by HPLC analysis. As seen in FIG. 3A, the compound of Formula II greatly reduces the degradation of atRA in the cells.

To investigate the specificity of our candidate to inhibit CYP26B1-mediated catabolism of atRA, COS-1 cells were transfected with CYP26B1 or an empty vector (in which case no CYP26B1 can be produced). COS-1 was maintained in Dulbecco's Modified Eagle's Medium (DMEM; Life Technologies, Carsbad, Calif., USA) and transfection of COS-1 was performed in 12 well plates using 1 μg/μl of CYP26B1 and 2 μl of lipofectamin 2000 in 250 μl of Opti-MEM (Opti-MEM: Modified Eagle's Minimum Essential Media; Life Technologies, Carlsbad, Calif., USA). The mixture was incubated at room temperature for 20 minutes and added to the plate for 4 h followed by addition of growth medium for 24 h. The next day, the medium was replaced by fresh DMEM and treated by 1 or 10 μM of the compound according to Formula II for 1 h followed by exposure to 1 μCl/ml of [³H] atRA for 2 h, and subsequent HPLC analysis. The transfection of the cells with CYP26B1 significantly reduced the levels of atRA compared to the control (empty vector), shown in FIG. 3B. Treatment of the transfected cells with 1 or 10 μM of the compound of Formula II again significantly increased the levels of atRA, indicating that the compound of Formula II has the ability to block CYP26B1-mediated catabolism of atRA.

Example 5. Effects of the New CYP26 Inhibitor on CYP26B1 Mediated at RA Catabolism To investigate the efficiency of the compound of Formula II in blocking CYP26B1, CYP26B1 was purified and subsequently incubated with 5 and 25 μM of compound of Formula II for different time points (10 s to 10 min). This experiment thus excludes any other possible metabolic route that potentially could have been present in the cellular experiments. Purified CYP26B1 was stored in buffer containing 50 mM $K_2HPO_4$, 0.5 mM EDTA and 20% of glycerol, pH 7.4 at −80° C. The assay was performed as follows: 5 nM of CYP26B1 and 10 nM oxidoreductase was preincubated. 5 or 25 µM of the compound of Formula II and 50 nM [$^3$H] atRA were added followed by addition of 1 mM NADPH in total volume of 100 µl of Kpi buffer and incubated for 10 sec to 10 min. The reaction was stopped by adding 100 µl absolute ethanol. The sample was subsequently extracted and analysed by HPLC. For control, experiments were performed as above but without initiation of the reaction by NADPH. As seen in FIG. 4, the compound of Formula II efficiently inhibited RA degradation at a concentration of 5 µM, fully consistent with the different cellular tests reported above.

The invention claimed is:

1. A compound of Formula I represented by:

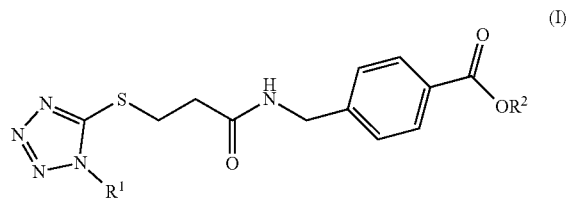

(I)

wherein $R^1$ represents hydrogen or a $C_{1-2}$ alkyl that is optionally substituted with one or more fluorine atoms;

wherein $R^2$ represents hydrogen or a carboxylic acid protecting group;

or a pharmaceutically acceptable salt thereof, provided that the compound or pharmaceutically acceptable salt thereof is not a compound of Formula II represented by:

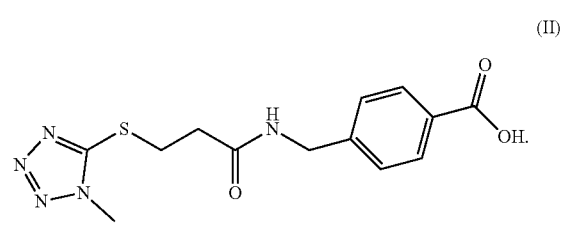 [SMILES: Cn1nnnc1SCCC(=O)NCc1ccc(C(=O)O)cc1]

(II)

2. The compound of Formula I according to claim 1, wherein $R^1$ is a methyl group, optionally substituted with one or more fluorine atoms.

3. The compound of Formula I according to claim 1, wherein $R^2$ is a carboxylic acid protecting group.

4. The compound of Formula I according to claim 3, wherein $R^2$ is said carboxylic acid protecting group and said carboxylic acid protecting group is selected from the group consisting of a $C_{1-4}$ alkyl, phenyl and benzyl.

5. A method of increasing the cellular level of endogenous all-trans retinoic acid (atRA) or reducing the degradation of exogenously added atRA, which method comprises administration of a therapeutically effective amount of a compound of Formula I represented by:

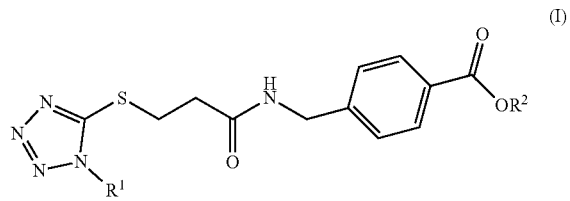

(I)

wherein $R^1$ represents hydrogen or a $C_{1-2}$ alkyl that is optionally substituted with one or more fluorine atoms;

wherein $R^2$ represents hydrogen or a carboxylic acid protecting group;

or a pharmaceutically acceptable salt thereof, to a subject in need thereof.

6. A pharmaceutical formulation comprising a compound of Formula I represented by:

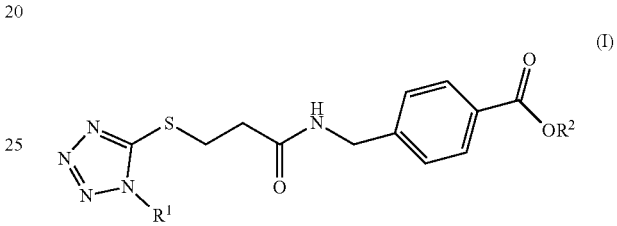

(I)

wherein $R^1$ represents hydrogen or a $C_{1-2}$ alkyl that is optionally substituted with one or more fluorine atoms;

wherein $R^2$ represents hydrogen or a carboxylic acid protecting group;

or a pharmaceutically acceptable salt thereof, in admixture with a pharmaceutically acceptable adjuvant, diluent, excipient or carrier.

7. The method according to claim 5, wherein the subject has a condition selected from a skin disorder; an undesirable growth or proliferation of cells; restenosis or thrombosis occurring upon the introduction of coronary stents; and inflammatory bowel disease.

8. A pharmaceutical formulation according to claim 6, wherein $R^1$ is a methyl group, optionally substituted with one or more fluorine atoms and $R^2$ is a carboxylic acid protecting group which is selected from the group consisting of a $C_{1-4}$ alkyl, phenyl and benzyl.

9. A pharmaceutical formulation according to claim 6, wherein said compound of Formula I is present in an amount of from 0.01 to 90% by weight of the formulation.

10. A pharmaceutical formulation according to claim 9, wherein said compound of Formula I is present in an amount of from 0.05 to 50% by weight of the formulation.

11. A pharmaceutical formulation according to claim 10, wherein said compound of Formula I is present in an amount of from 1 to 20% by weight of the formulation.

12. A pharmaceutical formulation according to claim 6, wherein the amount of the compound of Formula I in the formulation is sufficient to achieve serum levels of between about 1 pM and about 1 mM in a patient.

13. A pharmaceutical formulation according to claim 12, wherein the amount of the compound of Formula I in the formulation is sufficient to achieve serum levels of between about 10 pM and about 100 µM in a patient.

14. A pharmaceutical formulation according to claim 13, wherein the amount of the compound of Formula I in the formulation is sufficient to achieve serum levels of between about 100 pM and about 10 µM in a patient.

15. A pharmaceutical formulation according to claim 6 in a form suitable for oral, systemic, intratumoral, intradermal, subcutaneous, intraperitoneal, intracavitary, intraocular or intravenous injection, administration via drug eluting stent, or topical administration.

16. A pharmaceutical formulation according to claim 6 further comprising one or more compounds selected from: chelating agents, inhibitors of ferrochelatase, immunotherapeutic agents, angiogenesis inhibitors, surface penetration assisting agents, photosensitising agents, glucose, anti-cancer agents, anaesthetic or analgesic agents, retinoic acid and derivatives thereof, retinol and derivatives thereof, anti-inflammatory agents, blood pressure reducing agents, cytostatic compounds, antibiotic agents, and folic acid antagonists.

17. A graft stent, wherein a surface of the stent is at least partly coated with the pharmaceutical formulation according to claim 6.

18. A graft stent according to claim 17, wherein the amount of the compound of formula I in the stent coating is sufficient to achieve serum levels of between about 1 pM and about 1 mM in a patient.

19. A graft stent according to claim 18, wherein the amount of the compound of formula I in the stent coating is sufficient to achieve serum levels of between about 10 pM and about 100 μM in a patient.

20. A method of inhibiting restenosis following treatment of atherosclerosis in a patient, which method involves applying a graft stent of claim 17, to a patient in need thereof.

\* \* \* \* \*

UNITED STATES PATENT AND TRADEMARK OFFICE
CERTIFICATE OF CORRECTION

PATENT NO. : 10,577,333 B2
APPLICATION NO. : 16/076571
DATED : March 3, 2020
INVENTOR(S) : Eriksson et al.

Page 1 of 1

It is certified that error appears in the above-identified patent and that said Letters Patent is hereby corrected as shown below:

In the Specification

Column 10, Line 13: Please correct "10 µM" to read -- 10 pM --

Column 14, Line 32: Please correct "*P<0.05" to read -- *P≤0.05 --

In the Claims

Column 19, Line 29, Claim 20: Please correct "claim 17, to" to read -- claim 17 to --

Signed and Sealed this
First Day of September, 2020

Andrei Iancu
*Director of the United States Patent and Trademark Office*